US010349827B2

(12) United States Patent
Inoue et al.

(10) Patent No.: US 10,349,827 B2
(45) Date of Patent: Jul. 16, 2019

(54) VISION TESTING DEVICE AND HEAD-MOUNT TYPE DISPLAY DEVICE

(71) Applicant: CREWT MEDICAL SYSTEMS, INC., Tokyo (JP)

(72) Inventors: Satoshi Inoue, Tokyo (JP); Kenzo Yamanaka, Tokyo (JP); Shinji Kimura, Tokyo (JP)

(73) Assignee: CREWT MEDICAL SYSTEMS, INC., Tokyo (JP)

( * ) Notice: Subject to any disclaimer, the term of this patent is extended or adjusted under 35 U.S.C. 154(b) by 287 days.

(21) Appl. No.: 15/524,374

(22) PCT Filed: Oct. 22, 2015

(86) PCT No.: PCT/JP2015/079779
§ 371 (c)(1),
(2) Date: May 4, 2017

(87) PCT Pub. No.: WO2016/072272
PCT Pub. Date: May 12, 2016

(65) Prior Publication Data
US 2018/0271359 A1    Sep. 27, 2018

(30) Foreign Application Priority Data

Nov. 4, 2014    (JP) .................................. 2014-224181

(51) Int. Cl.
*A61B 3/10*        (2006.01)
*A61B 3/00*        (2006.01)
(Continued)

(52) U.S. Cl.
CPC ............ *A61B 3/005* (2013.01); *A61B 3/0058* (2013.01); *A61B 3/0091* (2013.01); *A61B 3/024* (2013.01);
(Continued)

(58) Field of Classification Search
CPC ..... A61B 3/005; A61B 3/0091; A61B 3/0058; A61B 3/14; A61B 3/152; A61B 3/032;
(Continued)

(56) References Cited

U.S. PATENT DOCUMENTS

| 2007/0200927 A1* | 8/2007 | Krenik ................... | A61B 3/032 348/47 |
| 2010/0016730 A1* | 1/2010 | Tanaka ................... | A61B 3/024 600/476 |
| 2014/0002796 A1* | 1/2014 | Marcos Munoz ... | G02B 27/017 351/206 |

FOREIGN PATENT DOCUMENTS

| JP | H07-67833 A | 3/1995 |
| JP | H11-225964 A | 8/1999 |

(Continued)

OTHER PUBLICATIONS

Jan. 19, 2016 International Search Report issued in International Patent Application No. PCT/JP2015/079779.

*Primary Examiner* — William R Alexander
*Assistant Examiner* — Henry A Duong
(74) *Attorney, Agent, or Firm* — Oliff PLC

(57) ABSTRACT

A head mount-type vision testing device, which is a head-mount type vision testing device mounted on a testee's head, including: a device main body having display devices for displaying a visual target for the testee and imaging devices for imaging eyeballs of the testee; a mounting fixture for mounting the device main body on the testee's head; and a controller that displays images of the eyeballs imaged by the imaging devices on the display devices, so that the testee can recognize a positional displacement state of the eyeballs caused by a positional displacement of the device main body mounted on the testee's head using the mounting fixture.

17 Claims, 8 Drawing Sheets

(51) Int. Cl.
  *A61B 3/024* (2006.01)
  *A61B 3/032* (2006.01)
  *A61B 3/15* (2006.01)
  *G02B 27/01* (2006.01)
  *A61B 3/14* (2006.01)
  *A61B 90/50* (2016.01)
(52) U.S. Cl.
  CPC ............... *A61B 3/032* (2013.01); *A61B 3/14* (2013.01); *A61B 3/152* (2013.01); *G02B 27/0172* (2013.01); *A61B 2090/502* (2016.02)
(58) Field of Classification Search
  CPC ..... A61B 3/024; A61B 2090/502; A61B 3/02; G02B 27/0172
  USPC ........................................................ 351/239
  See application file for complete search history.

(56) References Cited

FOREIGN PATENT DOCUMENTS

JP   2014-104174 A   6/2014
JP   2014-128493 A   7/2014

\* cited by examiner

VISION TESTING DEVICE AND HEAD-MOUNT TYPE DISPLAY DEVICE

TECHNICAL FIELD

The present invention relates to a vision testing device and a head-mount type display device.

DESCRIPTION OF RELATED ART

There is a "vision test" as one of eye tests, for testing a visual function of an eye. Also, there is a "visual field test" as a typical vision test. The visual field test is performed for diagnosis of visual field narrowing, visual field defect, and the like caused by, for example, glaucoma, retinal detachment and the like, and various testing devices have been proposed for this purpose.

Further, among conventional vision testing devices, there is a head-mount type vision testing device which is used by being mounted on a testee's head (for example, see patent documents 1 and 2). In this kind of vision testing device, when the vision testing device is mounted on the testee's head, for example, the vision testing device is tilted and a position of an eyeball of the testee is displaced from a specific predefined position in some cases. In this case, if the vision test is performed as it is, an accurate test result can not be obtained.

Therefore, for example patent document 1 teaches a technique of imaging an eyeball of a testee (referred to as "eye to be tested" hereafter) using a camera incorporated in a main body portion of the vision testing device (referred to as a "device main body" hereafter), and displaying an image of the eyeball thus obtained together with an alignment mark on a television monitor separate from the device main body. In this technique, an image of the eyeball imaged by the camera is displayed on a television monitor observed by a tester such as an ophthalmologist or an ophthalmologist, and a position of the device main body is adjusted so that a pupil of the testee is concentric with the alignment mark on the television monitor.

PRIOR ART DOCUMENT

Patent Document

Patent document 1: Japanese Patent Laid Open Publication No. 1995-67833
Patent document 2: Japanese Patent Laid Open Publication No. 2014-128493

SUMMARY OF THE INVENTION

Problem to be Solved by the Invention

However, in the technique described in the abovementioned patent document 1, when the main body portion of the vision testing device is mounted on the testee's head, the tester checks whether or not the device main body is properly mounted on the testee's head on a television monitor. Therefore, even though the device main body is mounted in a displaced state, the testee himself/herself cannot grasp this fact. Accordingly, in a positional adjustment of the device main body, the tester gives an instruction to the testee while watching the television monitor, and the testee moves the device main body in accordance with this instruction. In such a case, contents of the instruction such as a movement amount of the device main body and a direction of movement is sometimes not transmitted to the testee as intended by the tester. As a result, the testee moves the device main body in a direction not intended by the tester, or an amount of movement thereof is not appropriate in some cases, which sometimes took time to adjust the position of the device main body. In addition, since the tester has to keep watching the television monitor until the positional adjustment of the device main body is completed, there is also a disadvantage that other work can not be performed during that time.

A main object of the present invention is to provide the vision testing device capable of reducing a workload of the tester involved in the positional adjustment of the device main body when the main body portion of the vision testing device is mounted on the testee's head.

Means for Solving the Problem

According to a first aspect of the present invention, there is provided a vision testing device, which is a head-mount type vision testing device mounted on a testee's head, including:
a device main body having a display device for displaying a visual target for the testee and an imaging device for imaging an eyeball of the testee;
a mounting fixture for mounting the device main body on the testee's head; and
a controller that displays an image of the eyeball imaged by the imaging device on the display device, so that the testee can recognize a positional displacement state of an eyeball caused by a positional displacement of the device main body mounted on the testee's head using the mounting fixture.

According to a second aspect of the present invention, there is provided the vision testing device of the first aspect, wherein the controller sets a display frame on a display surface of the display device and displays an image of the eyeball imaged by the imaging device on the display frame.

According to a third aspect of the present invention, there is provided the vision testing device of the first aspect, wherein
the display device and the imaging device are separately provided for a left eye and a right eye of the testee,
the controller synthesizes an image of the left eye imaged by the imaging device for the left eye, and an image of the right eye imaged by the imaging device for the right eye so as to be arranged side by side, and the synthesized images of the left and right eyes are displayed on the display device for the left eye and the display device for the right eye, respectively.

According to a fourth aspect of the present invention, there is provided the vision testing device of the third aspect, wherein the controller sets two display frames side by side on the display surface of the display device for the left eye and the display surface of the display device for the right eye respectively, and displays the image of the left eye on a left-side display frame, and displays the image of the right eye on a right-side display frame viewed from the testee.

According to a fifth aspect of the present invention, there is provided the vision testing device of the third or fourth aspect, wherein the controller displays a fixation target to be gazed by the testee between the image of the left eye and the image of the right eye.

According to a sixth aspect of the present invention, there is provided the vision testing device of the second or fourth aspect, wherein the controller displays a mark in the display frame for aligning a position of a pupil of the eyeball.

According to a seventh aspect of the present invention, there is provided the vision testing device of any one of the first to sixth aspects, including:

a display optical system provided on an optical axis between an eyeball position where the eyeball of the testee is placed and the display device; and an observation optical system provided on an optical axis between the eyeball position and the imaging device, wherein the display optical system is formed by arranging a first lens, a mirror having wavelength selectivity, and a second lens group sequentially on the optical axis from the eyeball position to the display device, and the observation optical system is formed by arranging the first lens, the mirror, and a third lens sequentially on an optical axis form the eyeball position to the imaging device, and the optical axis from the eyeball position to the mirror is shared with the display optical system.

According to an eighth aspect of the present invention, there is provided a head-mount type display device, which is a head-mount type vision testing device mounted on a user's head, including:

a device main body having a display device for displaying an image for the user, and an imaging device for imaging an eyeball of the user;

a mounting fixture for mounting the device main body on the user's head; and a controller that displays an image of the eyeball imaged by the imaging device on the display device, in order that the user can recognize a positional displacement state of an eyeball caused by a positional displacement of the device main body mounted on the user's head using the mounting fixture.

Advantage of the Invention

According to the present invention, a workload of a tester involved in a positional adjustment of a device main body can be reduced, when the device main body of a vision testing device is mounted on a testee's head.

DETAILED DESCRIPTION OF THE INVENTION

Figure 1:
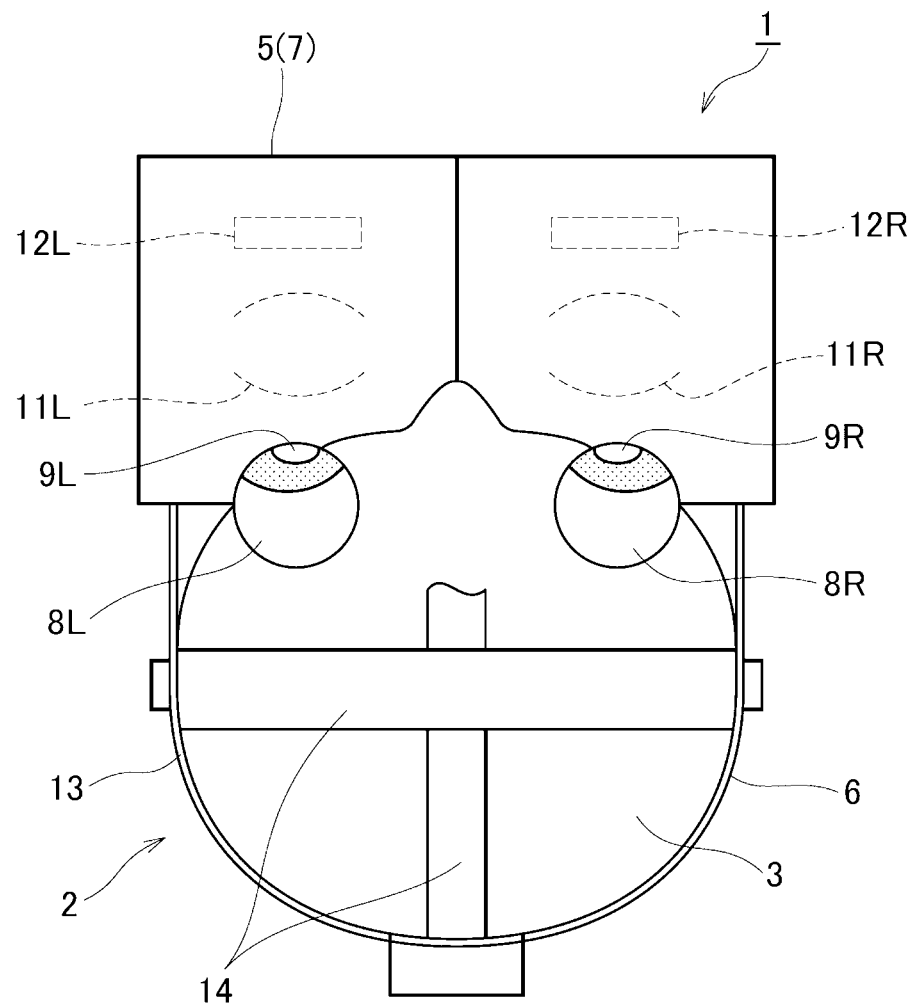
FIG. 1 is a schematic view of a vision testing device according to an embodiment of the present invention.

Embodiments of the present invention will be described hereafter in detail, with reference to the drawings.

In the description of the embodiments of the present invention, explanation will be given in the following order.

1. Configuration of a vision testing device
2. Vision testing method based on a vision testing mode
3. Positional adjustment method of a device main body based on an alignment mode
4. Effect of an embodiment
5. Other embodiment
6. Modified example, etc.

<1. Configuration of a Vision Testing Device>

FIG. 1 is a schematic view of a vision testing device according to an embodiment of the present invention.

A vision testing device 1 shown in the figure is a head-mount type vision testing device used by being mounted on a head 3 of a testee 2. The vision testing device 1 roughly includes a device main body 5 and a mounting fixture 6 mechanically connected to the device main body 5.

The device main body 5 includes a casing 7 having a space inside. An internal space of the casing 7 is divided into left and right. This is because a vision test is performed separately for a left eye 8L and a right eye 8R of a testee 2. In this vision test, when the left eye 8L is used as the eye to be tested, the testee 2 views a visual target through a pupil 9L of the left eye 8L, and when the right eye 8R is used as the eye to be tested, the testee 2 views the visual target through the pupil 9R of the right eye 8R.

The term "visual target" described here is displayed for giving a stimulus by light to the eyeball of the testee when testing a vision of the testee. Regarding the visual target, there is no particular limitation on size, shape, etc. For example, at the time of glaucoma test, it is possible to test (identify) the presence or absence of a missing field of view and a location of the defect by displaying a point of light with a predetermined size as a visual target and changing a position of the point of the light.

In one space of the casing 7, a display optical system 11L and a display device 12L are provided. In the other internal space of the casing 7, a display optical system 11R and a display device 12 R are provided. The display optical system 11L and the display device 12L perform the vision test for the left eye 8L of the testee 2. The display optical system 11R and the display device 12R are provided for performing the vision test for the right eye 8R of the testee 2. The distance between the optical axes of the left and right display optical systems 11L and 11R can be adjusted in accordance with a distance between the pupils of the testee 2 by an adjustment mechanism (not shown).

The mounting fixture 6 is provided for mounting the device main body 5 on the head 3 of the testee 2. The mounting fixture 6 has a belt 13 wound in a U-shape from both side heads of the testee 2 to a rear head, and a belt 14 wound around a head top of the testee 2. The mounting fixture 6 has a mechanism such that by pulling and tightening the belt 13 from the rear head side, with the length of the belt 14 adjusted appropriately, the device main body 5 can be mounted on the head 3 of the testee 2.

A distance between the optical axes of the display optical systems 11L and 11R, is adjusted so as to correspond to the inter-pupil distance in a state where the testee 2 faces the front, after the device main body 5 is fixed to the head 3 of the testee 2 by the mounting fixture 6.

In the description hereafter, when the left eye 8L and the right eye 8R of the testee 2 are described without distinction between left and right, they are collectively referred to as the eyeball 8 and the pupil 9 by omitting reference letters L and R respectively. Likewise, when the display optical systems 11L, 11R and the display devices 12L, 12R are described without distinction between the device for the left eye and the device for the right eye, they are collectively referred to as the display optical system 11 and the display device 12 by omitting reference letters L and R, respectively.

Figure 2:
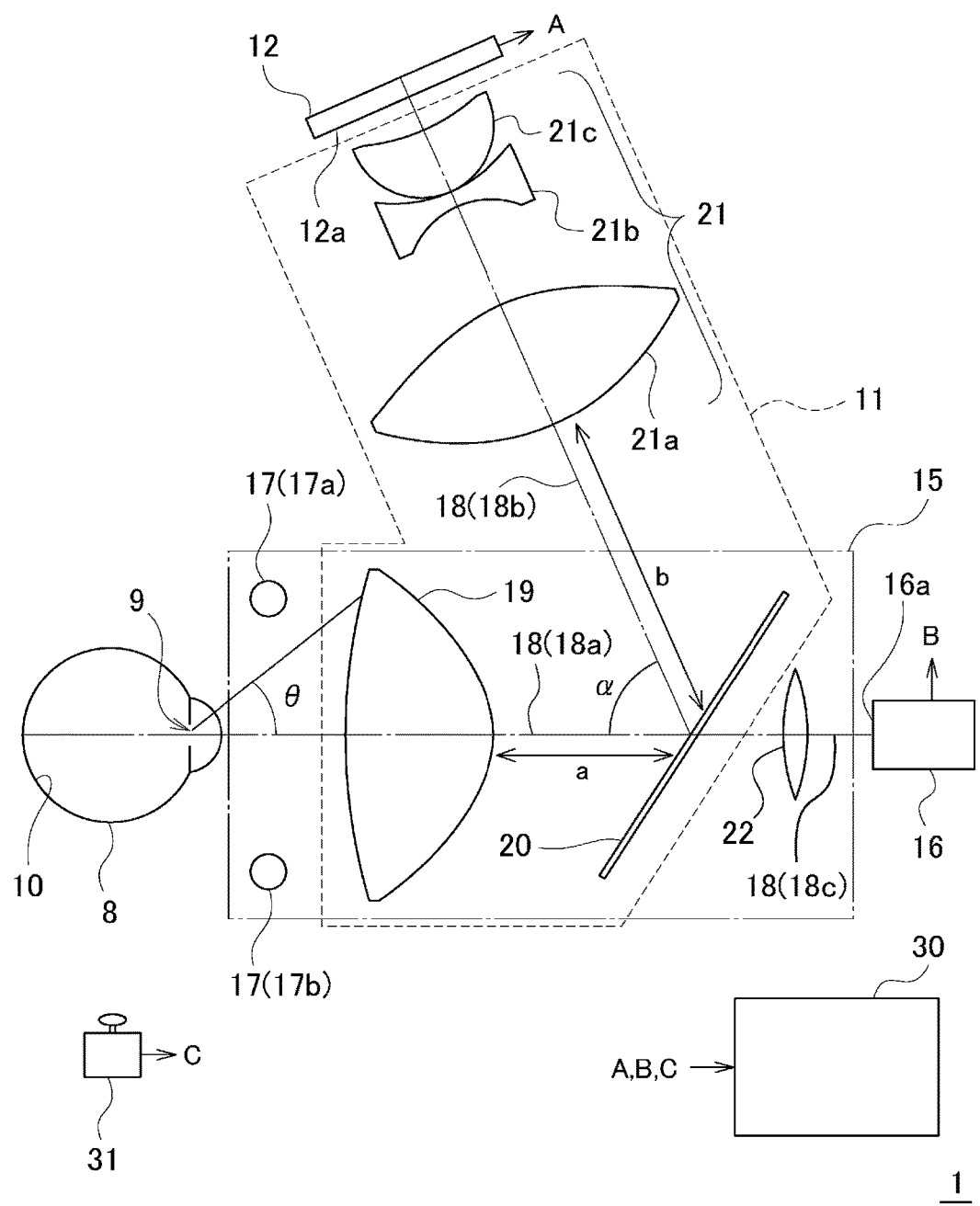
FIG. 2 is a schematic view including configurations of an optical system and a control system of the visual testing device according to an embodiment of the present invention.

FIG. 2 is a schematic view including configurations of an optical system and a control system of the vision testing device according to an embodiment of the present invention.

As shown in the figure, in addition to the abovementioned display optical system 11 and the display device 12, the vision testing device 1 includes an observation optical system 15 for observing the eyeball 8 of the testee, an imaging device 16 for imaging the eyeball 8 of the testee through the observation optical system 15, an infrared light source 17 for radiating an infrared ray to the eyeball 8 of the testee, a controller 30 that controls an entire body of the vision testing device 1, and a response switch 31. The observation optical system 15, the imaging device 16, and the infrared light source 17 are provided separately for the left eye and the right eye of the testee, similarly to the display optical system 11 and the display device 12 described above, and a control unit 30 and a response switch 31 are provided for each vision testing device 1, one by one.

The display optical system 11 is provided on the optical axis 18 between the eyeball position where the eyeball 8 of the testee is placed and the display surface 12a of the display device 12. Specifically, the display optical system 11 has a configuration in which a first lens 19, a mirror 20, and a second lens group 21 are arranged in an order from the eyeball position side of the testee. Each constituting element will be described hereafter. In the description hereafter, an optical axis from the eyeball position to the mirror 20 is defined as an optical axis 18a, and an optical axis from the mirror 20 to the display device 12 is defined as an optical axis 18b, out of the optical axis 18 from the eyeball position of the testee to the display device 12.

The first lens 19 is arranged on the optical axis 18a from the eyeball position to the mirror 20. The first lens 19 is formed using an aspheric lens (convex lens) having a positive power. The first lens 19 causes a light reflected by the mirror 20 and incident on the first lens 19 to be converged into the pupil 9 of the testee, while suppressing a dispersion of the light when the testee views an object through the pupil 9 at a wide angle. In FIG. 2, when a point of light serving as a visual target is displayed on the display surface 12a of the display device 12, and the testee views this visual target through the display optical system 11 from the eyeball position, an incident angle of the principal ray incident on the first lens 19 from a center of pupil of the testee is indicated by a symbol $\theta$. The incident angle $\theta$ is an angle with respect to the optical axis 18a (the angle formed by the principal ray passing through the center of the pupil and the optical axis 18a). An outer diameter (diameter) and a position of the first lens 19 on the optical axis 18a are set under conditions capable of securing at least a viewing angle required for a vision test. Specifically, a maximum viewing angle (maximum value of $\theta$) of the display optical system 11 using the first lens 19, is preferably set in a range of not less than 30 degrees and not more than 60 degrees in a case of half angle of view (60 degrees or more and 120 degrees or less in a case of a full angle of view).

The mirror 20 is arranged on the optical axis 18a from the eyeball position to the mirror 20 on the side opposite to the eyeball position with the first lens 19 interposed therebetween. The mirror 20 is configured using a mirror having wavelength selectivity. Specifically, the mirror 20 is configured by using a cold mirror that reflects a visible light and transmits an infrared ray. A tilt of a reflecting surface of the mirror 20 with respect to the optical axis 18a is set such that the angle $\alpha$ between the optical axis 18a bent by the mirror 20 and the optical axis 18b is preferably less than 90 degrees, more preferably less than 80 degrees, and more preferably in a range of "40 degrees<$\alpha$<70 degrees".

Here, in a case of $\alpha \leq 40°$, there is a possibility that the display device 12 and the second lens group 21 are too close to the testee's head, and they interfere with the head. In contrast, in a case of $\alpha > 40°$, interference of the display device 12 and the second lens group 21 with the head can be avoided. On the other hand, in a case of $\alpha \geq 90°$, when the testee tilts the head forward, the vision testing device 1 is likely to fall-off from the head. In contrast, in a case of $\alpha < 90°$, when the testee tilts the head forward, the vision testing device 1 is less likely to fall-off from the head.

The second lens group 21 is arranged on the optical axis 18b from the mirror 20 to the display device 12. The second lens group 21 is configured using three lenses 21a, 21b, and 21c. The three lenses 21a, 21b, and 21c are sequentially arranged from the mirror 20 side toward the display device 12 side. In other words, the lens 21a is arranged at the position closest to the mirror 20 on the optical axis 18b, and the lens 21c is arranged at the position closest to the display device 12 on the optical axis 18b. A lens 21b is disposed between the two lenses 21a and 21c. Then, the lens 21b is arranged near the lens 21c in a state of being separated from the lens 21a.

The lens 21a is configured using an aspheric lens (convex lens) having a positive power. In addition, the lens 21b is configured using an aspherical lens (concave lens) having a negative power, and the lens 21c is configured using an aspheric lens (convex meniscus lens) having a positive power. The outer diameter (diameter) of the lens 21a is larger than outer diameters of the other lenses 21b and 21c, and outer diameters of the lenses 21b and 21c are substantially equal to each other.

Here, when the Abbe number of the material of the first lens 19 is v1, the first lens 19 is made of a material (glass, plastic, etc.) that satisfies the relational expression "45<v1<80". On the other hand, when the Abbe numbers of the lenses 21a and 21c having positive powers among the lenses 21a to 21c constituting the second lens group 21 are both v2, each lens 21a, 21c is made of a material satisfying the relational expression "45<v2<80". Further, when the Abbe number of the lens 21b having a negative power is v3, the lens 21b is made of a material satisfying the relational expression "15<v3<30".

Further, when the focal length of the first lens 19 is f1 and the focal length of the second lens group 21 is f2, they satisfy the relational expression "0<f1/f2<1.0". Further, the focal length f1 of the first lens 19 is shorter than the sum (a+b) of an optical distance a from the first lens 19 to the mirror 20 and an optical distance b from the mirror 20 to the second lens group 21 (lens 21 a).

The display device 12 is arranged so as to face the lens 21c of the second lens group 21 on the optical axis 18b from the mirror 20 to the display device 12. The display device 12 is configured using, for example a planar display device such as a liquid crystal display device having a backlight. The display surface 12a of the display device 12 has a configuration in which a large number of pixels are arranged in a matrix. Then, when actually displaying an image (including a visual target) on the display surface 12a, display (ON) and non-display (OFF) of the image can be controlled on a pixel basis. The display surface 12a of the display device 12 preferably has a display size with a diagonal length of 1.5 inches or less, more preferably a display size with a diagonal length of 1 inch or less, and the optical axis 18b is aligned with a center of the display surface 12a.

In the display optical system 11 and the display device 12 having the above configuration, when the visual target is displayed on the display surface 12a of the display device 12, the testee 2 views the target from the eyeball position through the first lens 19, the mirror 20, and the second lens group 21. In this case, by increasing the outer diameter of the first lens 19 closest to the eyeball position, the vision test can be performed in a wider range. However, when the outer diameter of the first lens 19 is increased, the principal ray passing through the lens end is greatly tilted with respect to the optical axis 18 (18a). Therefore, in a case of a low power of the first lens 19, the principal ray passing through the lens end is dispersed.

Therefore in this embodiment, the principal ray passing through the lens end of the first lens 19 is largely refracted and is converged on the reflecting surface of the mirror 20 by using the lens having a high power (preferably a power of 20 D (diopter) or more and 60 D or less) for the first lens 19. However, when the high power first lens 19 is used as described above, the light flux of the principal ray is collected and focused on the way of the optical path from the first lens 19 to the second lens group 21. Therefore, in order to collect (form the image of) the light flux of the principal ray which is focused on the way of the optical path on the display surface 12a of the display device 12, the second lens group 21 is arranged on the optical axis 18b. Further, in order to correct chromatic aberration and image magnification, the second lens group 21 is composed of three lenses 21a, 21b, and 21c.

The observation optical system 15 is provided for observing an anterior ocular part including a pupil 9, an iris, a sclera, or the like, or a fundus oculi including a retina 10 for example, with the eyeball 8 of the testee as the observation target. The observation optical system 15 is provided on the optical axis 18 from the eyeball position of the testee to the imaging device 16. Specifically, the observation optical system 15 has a configuration in which the first lens 19, the mirror 20, and the third lens 22 are arranged in an order from the eyeball position side of the testee. Among them, the first lens 19 and the mirror 20 including the optical axis 18a are shared (shared) with the display optical system 11 described above. Also, when the optical axis from the mirror 20 to the imaging device 16 is the optical axis 18c, the optical axis 18c is substantially parallel to the abovementioned optical axis 18a.

The third lens 22 is arranged on the optical axis 18c from the mirror 20 to the imaging device 16. The third lens 22 is configured using an aspheric lens (convex lens) having a positive power. When observing the eyeball 8 using the first lens 19 as an objective lens, the third lens 22 forms the image of the light incident on the first lens 19 from the eyeball 8 and transmitted through the mirror 20, on the imaging surface 16a of the imaging device 16.

The imaging device 16 images an eyeball (anterior ocular part, fundus oculi etc.) 8 to be tested. The imaging device 16 is configured using a CCD (Charge Coupled Device) imaging device, a CMOS (Complementary Metal Oxide Semiconductor) imaging device, and the like having sensitivity to infrared rays. The imaging surface 16a of the imaging device 16 is arranged on the optical axis 18c in a direction facing the eyeball 8, and the optical axis 18c is aligned with a center of the imaging surface 16a.

The infrared light source 17 radiates infrared rays toward the eyeball position of the testee. The infrared light source 17 is configured using a pair of infrared light emitting diodes 17a and 17b. The pair of infrared light emitting diodes 17a and 17b are arranged obliquely upward and obliquely downward of the eyeball position of the testee so as not to obstruct the field of view of the testee. Then, the infrared light source 17 has a configuration in which one infrared light emitting diode 17a radiates infrared rays from obliquely upward of the eyeball 8 of the testee and the other infrared light emitting diode 17b radiates infrared rays from obliquely downward of the eyeball 8 of the testee.

In the observation optical system 15 and the imaging device 16 having the abovementioned configuration, the imaging device 16 images the image of the eyeball 8 through the first lens 19, the mirror 20, and the third lens 22 while radiating infrared rays from the infrared light source 17 to the eyeball 8 of the testee.

The controller 30 realizes various functions (means) in performing the vision test. For example, the controller 30 has a casing structure smaller than that of the device main body 5, and is arranged to be mounted on the rear head side of the mounting fixture 6. Thereby, a weight balance in the front and rear of the device body 5 and the controller 30, can be maintained.

The controller 30 is configured by a computer including a combination of a CPU (Central Processing Unit), RAM (Random Access Memory), ROM (Read Only Memory), HDD (Hard Disk Drive), and various interfaces, etc. Then, the controller 30 is configured to realize various functions by executing a predetermined program stored in ROM or HDD. The predetermined program for realizing each function is installed in a computer and used, but before the installation, it may be provided by being stored in a computer readable storage medium, or may be provided through a communication line connected to the computer.

The controller 30 has an operation control function and an image processing function as an example of a function (means) realized by executing the program. The operation control function is a function of controlling an operation of each part such as the display device 12, the imaging device 16, the infrared light source 17, etc. incorporated in the device main body 5. The image processing function is a function of applying various image processing to the image of the eyeball 8 imaged by the imaging device 16. The image of the eyeball 8 imaged by the imaging device 16 is captured into the controller 30 in the form of electronic data (hereinafter also referred to as "image data"). An instruction signal for operation control and image data of the eyeball 8 are exchanged via a wired or wireless communication line.

The controller 30 has at least two modes as a mode for operation control. One is an alignment mode and the other is a vision testing mode. Among them, the alignment mode is performed for a positional adjustment of the device main body 5. Specifically, the alignment mode is a mode for adjusting (correcting) a position of the device main body 5 when the position of the device main body 5 mounted on the head 3 of the testee 2 using the mounting fixture 6, is displaced from a regular position as shown in FIG. 1. "Regular position" described here refers to a position suitable for the vision test. The vision testing mode is a mode for performing the vision test by presenting the visual target to the testee. Specific contents of a vision testing method based on the vision testing mode will be described later.

An operation control mode may be switched by the following configuration, for example. That is, an external terminal device is communicably connected to the controller 30 by wireless or wire. Then, a mode switching signal is inputted from the terminal device to the controller 30, so that the controller 30 switches the operation control mode according to the mode switching signal. The alignment mode is basically performed before the vision testing mode. However, as necessary, the alignment mode may be performed in the middle of the vision testing mode or after the end of the vision testing mode. This is because, it is conceivable that for example when the testee touches the device main body 5 or moves the head 3 suddenly during the visual test performed in the vision testing mode, the position of the device main body 5 is displaced.

The response switch 31 is a switch whose switching operation is performed by the testee. When the testee pushes the response switch 31, an ON signal is outputted from the response switch 31 at that moment. This ON signal is captured into the controller 30. The response switch 31 is a manual type operated by the testee by holding it in his/her hand. However, the response switch 31 is not limited thereto, and a foot-operated switch may also be used.

Figure 3:
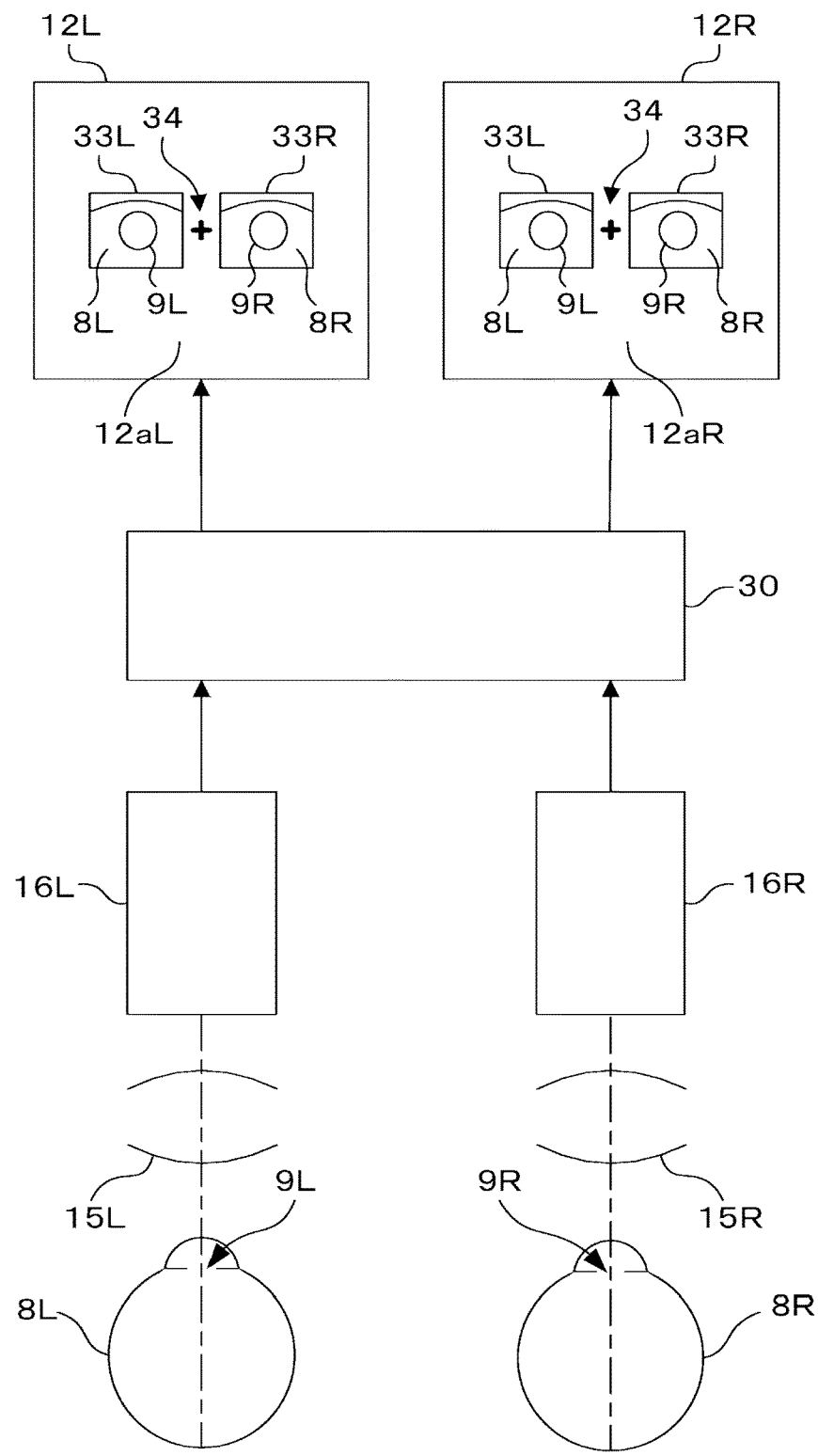
FIG. 3 is a schematic view showing a state when the vision testing device is operated in an alignment mode.

FIG. 3 is a schematic view showing a state when the vision testing device is operated in the alignment mode.

In the alignment mode, in order that the testee 2 can recognize a positional displacement state of the eyeball 8 caused by the positional displacement of the device main body 5 mounted on the head 3 of the testee using the mounting fixture 6, the controller 30 captures the image of the eyeball 8 imaged by the imaging device 16 and displays the image on the display device 12. At this time, the image of the eyeball 8 displayed on the display device 12 is a real-time moving image. The positional displacement state of the eyeball 8 refers to the presence or absence of a positional displacement such as whether or not the position of the eyeball 8 is displaced from the predetermined position, a direction of the positional displacement, an amount of the positional displacement, and the like. In order that the testee 2 can recognize the positional displacement state of the eyeball 8, the controller 30 displays images of both left and right eyes per one display device 12. Detailed description will be given hereafter.

The controller 30 captures an image of the left eye 8L imaged by the imaging device 16L and an image of the right eye 8R imaged by the imaging device 16R, and synthesizes captured images of the left eye 8L and the right eye 8R, so as to be arranged side by side. In this synthesis processing, the controller 30 arranges and sets the two display frames 33L, 33R side by side on a display surface 12aL of the display device 12L. In other words, two display frames 33L and 33R are set on one display surface 12aL. Then, the controller 30 synthesizes the images so that the image of the left eye 8L is assigned to the left-side display frame 33L viewed from the testee 2 who is wearing the device main body 5 on the head 3, while the image of the right eye 8R is assigned to the right-side display frame 33R viewed from the testee 2. Similarly, the controller 30 arranges and sets the two display frames 33L, 33R side by side on a display surface 12a of the display device 12R, and synthesizes the images so that an image of the left eye 8L and an image of the right eye 8R are assigned to the display frames 33L and 33R respectively.

In the above synthesis processing, the two display frames 33L and 33R are set as follows according to a positional relationship between the display device 12 and the imaging device 16 with respect to the optical axis 18. That is, left and right display frames 33L and 33R are set so that the pupil 9L of the left eye 8L imaged by the imaging device 16L is positioned at the center of the display frame 33L, and the pupil 9R of the right eye 8R imaged by the imaging device 16R is positioned at the center of the display frame 33R, when the device main body 5 is properly mounted on the head 3 of the testee 2 and the testee 2 looks straight ahead using both left and right eyes. In one display frame 33, the pupil 9 and the iris around the pupil 9 are mainly displayed among the images of the eyeball 8 imaged by the corresponding imaging device 16. Further, on one display surface 12a, the part of the display frame 33 and the part of the fixation target 34 which will be described later are displayed with appropriate brightness respectively, but the other parts are not displayed (the display of the image is turned off).

The controller 30 displays the images obtained by the synthesis processing, on both the display device 12L and the display device 12R. Thereby, a synthesized image including the image of the left eye 8L and the image of the right eye 8R is displayed on the display device 12L, and the same synthesized image is also displayed on the display device 12R.

Figure 4:
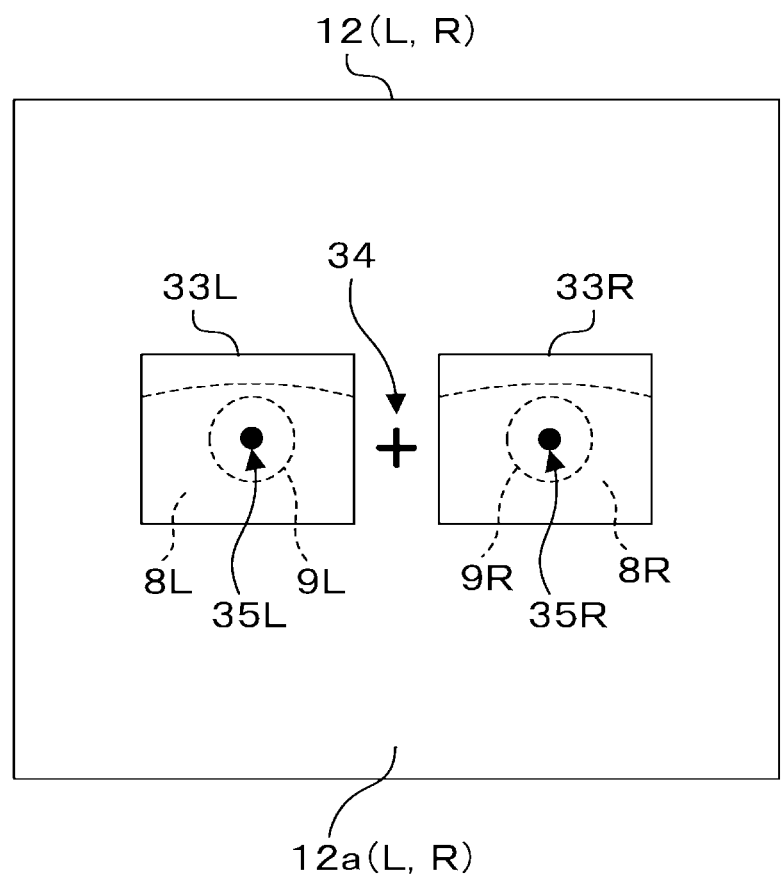
FIG. 4 is a view showing a state in which marks are displayed in a display frame.

At that time, as necessary, the controller 30 displays a mark 35 in the display frame 33 for aligning the position of the pupil 9 of the eyeball 8 as shown in FIG. 4. Specifically, the mark 35L is displayed at the center of the left display frame 33L and the mark 35R is displayed at the center of the right display frame 33R. The mark 35 is displayed so as to be superimposed on the image of the eyeball 8 in the display frame 33. Whether or not to display the mark 35 can be switched depending on a condition setting of the vision test device 1.

Further, the controller 30 displays (presents) a fixation target 34 on each of the display surfaces 12aL and 12aR so as to be gazed by the testee 2. The fixation target 34 has, for example a cross shape, and is displayed between the two display frames 33L and 33R (Intermediate portion) so as not to overlap with the left and right display frames 33L and 33R. As a result, the fixation target 34 is displayed between the image of the left eye 8L and the image of the right eye 8R, when the image of the left eye 8L is displayed on the left display frame 33L viewed from the testee 2 and the image of the right eye 8R is displayed on the right display frame 33R viewed from the testee 2. Further, the fixation target 34 is displayed at the center of each display surface 12aL, 12aR (the portion where the optical axis 18b is aligned).

An operation of the vision testing device 1 according to an embodiment of the present invention will be described next.

Here, the vision testing method based on the vision testing mode will be described first, and then a positional adjustment method of the device main body based on the alignment mode will be described.

<The Vision Testing Method Based on the Vision Testing Mode>

In the vision testing device 1 having the abovementioned configuration, it is possible to perform dynamic quantitative visual field test (Goldman visual field test), static quantitative visual field test, fundus visual field test (microperimetry), electroretinogram (ERG) and other test. Here, as an example, a case of performing a static quantitative visual field test will be described.

The static quantitative visual field test is performed as follows. First, the visual target is presented at one point in the visual field, and its brightness is gradually increased. Then, when the brightness of the visual target reaches a certain level, the visual target becomes visible from the testee. A value corresponding to the brightness at the time point visible from the testee is set as retina sensitivity at the point of the visual target which is presented at that time. Then, by performing a similar measurement for each point in the field of view, the difference in retina sensitivity within the visual field is quantitatively investigated and a map is created. Such a static quantitative visual field test includes a subjective test and an objective test. By using the vision testing device 1 of this embodiment, any type of test can be performed. Explanation will be given hereafter.

The subjective test is performed as follows. First, the head-mount type vision testing device 1 is mounted on the testee's head, so that the testee holds the response switch 31. Next, based on a command from the controller 30, the visual target for the vision test is displayed at one point on the display surface 12a of the display device 12. At this time, at first, the brightness of the visual target is made dark, and thereafter, the brightness of the visual target is gradually increased. Then, even if the target is not visible from the testee at first, when the brightness of the visual target reaches a certain level, the retina of the testee responds to a light stimulus, and the visual target becomes visible from the testee. Therefore, when the visual target becomes visible from the testee, the testee is asked to push the response switch 31. When the testee pushes the response switch 31, an ON signal is sent to the controller 30. Upon receipt of this ON signal, the controller 30 performs a predetermined processing, and sets the value corresponding to the brightness of the point of the visual target at that time as the retina sensitivity at that point. Thereafter, a similar measurement is performed for each point within the field of view to quantitatively investigate the difference in retina sensitivity within the field of view and a retina sensitivity map is created.

The objective test is performed as follows. First, the head-mount type vision testing device 1 is mounted on the testee's head. In this case, the testee is not required to hold the response switch 31. Next, based on the command from the control unit 30, the visual target for the visual field test is displayed at one point on the display surface 12a of the display device 12. At this time, at first, the brightness of the visual target is made dark, and thereafter, the brightness of the visual target is gradually increased. Then, even if the target is not visible from the testee at first, when the brightness of the visual target reaches a certain level, the retina of the testee responds to a light stimulus, and the visual target becomes visible from the testee.

At that time, a size (pupil diameter) of the pupil 9 of the testee is changed according to the brightness of the visual target. Specifically, the diameter of the pupil 9 of the testee is reduced. At this time, state change of the eyeball 8 is imaged. The eyeball 8 is imaged by radiating the infrared ray toward the eyeball 8 from the infrared light source 17, thereby obtaining an image of the light of the eyeball 8, and forming this image on the imaging surface 16a of the imaging device 16 through the observation optical system 15 (19, 20, and 22). The timing for starting imaging of the eyeball 8 may be set, for example at a timing before the visual target is displayed on the display surface 12a, or at the same time as display of the visual target. Incidentally, since the human retina is not sensitive to the infrared ray, it does not affect the state change of the eyeball 8.

Image data of the eyeball 8 imaged using the imaging device 16 is captured into the controller 30. The controller 30 judges whether a pupil diameter of the testee has changed (reduced) in response to the brightness of the target based on the image data sent from the imaging device 16 in a process of gradually increasing the brightness of the visual target. Then, when it is judged that the pupil diameter of the testee has changed, a value corresponding to the brightness of the point of the visual target at that time is set as the retina sensitivity at that point. Thereafter, a similar measurement are automatically performed one after another for each point in the field of view to quantitatively investigate the difference in retina sensitivity in the field of view, and a retina sensitivity map is automatically created.

Further, in the objective test, it is possible to use a single threshold upper stimulation method of displaying a bright target at one point on the display surface 12a of the flat display device 12, and observing the degree of reduction of the pupil diameter, so that the sensitivity map is created.

<3. Method for Adjusting the Position of the Device Main Body Based on the Alignment Mode>

In the vision testing device 1 having the abovementioned configuration, prior to the start of the vision test, the positional adjustment of the device main body 5 mounted on the head 3 of the testee 2 is performed as follows.

First, as described above, the controller 30 synthesizes the image of the left eye 8L imaged by the imaging device 16L and the image of the right eye 8R imaged by the imaging device 16R, and adds the fixation target 34 to the synthesized image and displays it on the display device 12L and the display device 12R. At this time, the image of the left eye 8L and the mark 35L are displayed in the left-side display frame 33L, and the image of the left eye 8L and the mark 35L are displayed in the right-side display frame 33R in two display frames 33L and 33R set on the display surface 12aL of the display device 12L. As a result, the testee 2 who is wearing the device main body 5 on the head 3 simultaneously views the same image (synthesized image) by the left eye 8L and the right eye 8R. At this time, if the distance between the left and right optical axes is appropriately adjusted, the image viewed by the left eye 8L and the image viewed by the right eye 8R are viewed to be perfectly overlapped. Therefore, in the brain of the testee 2, the image displayed on the display device 12L and the image displayed on the display device 12R are recognized as a single integrated image.

In such a situation, the tester gives an instruction to the testee 2 to gaze the fixation target 34 displayed between the left and right two display frames 33L and 33R. Thus, a line of sight of both eyes of the testee 2 is fixed in a state directed straight forward. Under such a fixation state, the tester asks the testee to check which part of the left-side display frame 33L displays the pupil 9L of the left eye 8L of the testee, and which part of the right-side display frame 33R displays the pupil 9R of the right eye 8R of the testee. Then, when the pupil 9L of the left eye 8L is displaced from the center of the display frame 33L or the pupil 9R of the right eye 8R is displaced from the center of the display frame 33L, the tester gives an instruction to the testee to properly move the device main body 5 so as to solve the displacement. Several typical examples of the positional adjustment of the device main body 5 will be described below.

(First Typical Example)

Figure 5:
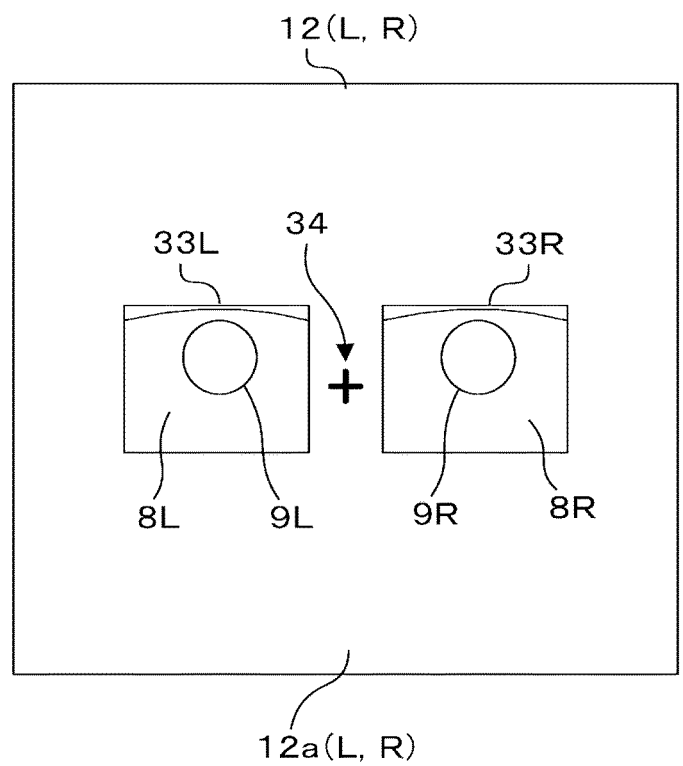
FIG. 5 is a view showing a first typical example relating to a positional adjustment of a device main body.
Figure 6:
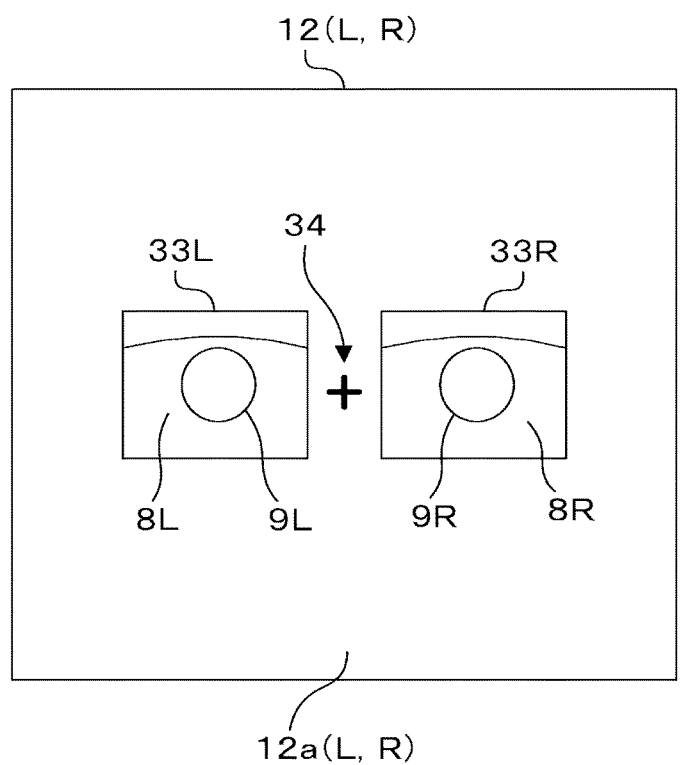
FIG. 6 is a view showing a state after the positional adjustment of the device main body.

A first typical example is a case where the device main body 5 is mounted in a displaced state upward or downward. In this case, for example, when the position of the device main body 5 is displaced downward, as shown in FIG. 5, the positions of the pupils 9L, 9R displayed in the left and right display frames 33L, 33R are displaced upward viewed from the testee 2. In order to correct such a displacement, the testee moves the device man body 5 upward. As a result, positions of the pupils 9L, 9R are moved downward as seen from the testee 2 in the left and right display frames 33L, 33R in conjunction with a movement of the device main body 5. Accordingly, by moving the device main body 5 while checking the positions of the pupils 9L and 9R displayed in the left and right display frames 33L and 33R, as shown in FIG. 6, the testee 2 can adjust the position of the device main body 5 so that the pupils 9L and 9R are positioned at the center of the left and right display frames 33L and 33R, respectively.

(Second Typical Example)

Figure 7:
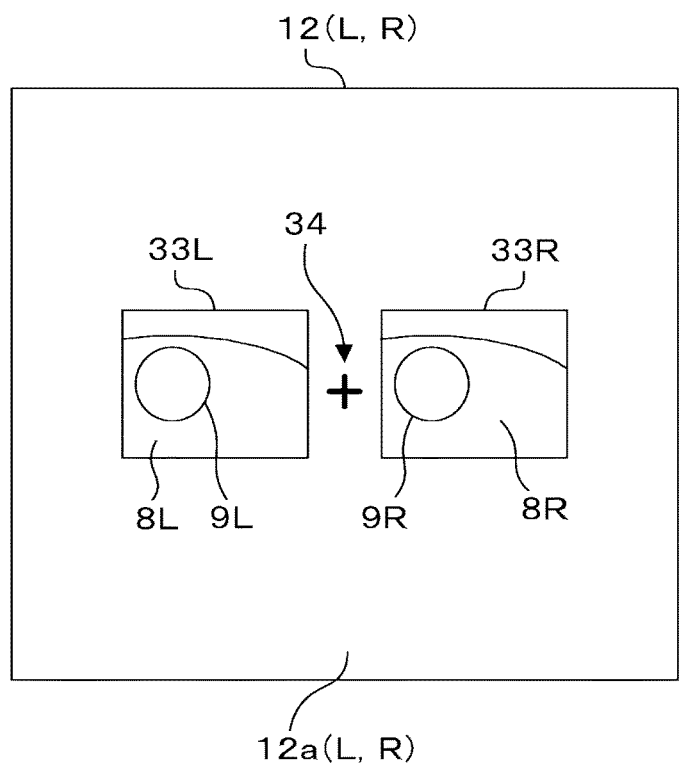
FIG. 7 is a view showing a second typical example relating to the positional adjustment of the device main body.

A second typical example is a case where the device main body 5 is mounted so as to be displaced to either the left or right-side. In this case, for example when the position of the device main body 5 is displaced toward the right-side head of the testee 2, as shown in FIG. 7, positions of the pupils 9L and 9R displayed in the left and right display frames 33L and 33R are displaced to the left-side viewed from the testee 2. When this displacement is corrected, the testee 2 moves the device main body 5 to the left-side head. As a result, positions of the pupils 9L and 9R move to the right-side as viewed from the testee 2 in the left and right display frames 33L and 33R in conjunction with the movement of the device main body 5, respectively. Accordingly, by moving the device main body 5 while checking the positions of the pupils 9L and 9R displayed in the left and right display frames 33L and 33R, as shown in FIG. 6, the position of the device main body 5 can be adjusted so that the pupils 9L and 9R are positioned at the center of the left and right display frames 33L and 33R, respectively.

(Third Typical Example)

Figure 8:
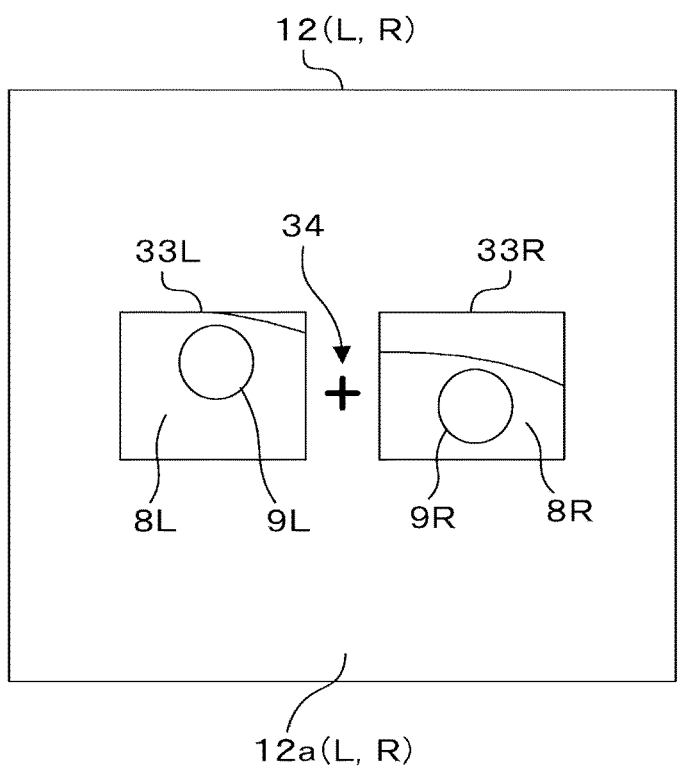
FIG. 8 is a view showing a third typical example relating to the positional adjustment of the device main body.

A third typical example is a case where the device main body 5 is tilted with respect to a horizontal reference line passing through the centers of the pupils of the right and left eyes of the testee. In this case, for example, if the device main body 5 is tilted in such a direction that the right-side head of the testee 2 is high and the left-side head of the testee 2 is low, as shown in FIG. 8, the position of the pupil 9L displayed in the left-side display frame 33L is displaced upward viewed from the testee 2 and the position of the pupil 9R displayed in the right-side display frame 33R is displaced downward viewed from the testee 2. When this displacement is corrected, the testee 2 moves the device main body 5 so as to lower the right-side head and raise the left-side head. Thus, in conjunction with the movement of the device main body 5, the position of the pupil 9L is moved downward viewed from the testee 2 in the left display frame 33, and the position of the pupil 9R is moved upward viewed from the testee 2 in the right-side display frame 33R. Accordingly, by moving the device main body 5 while checking the positions of the pupils 9L and 9R displayed in the left and right display frames 33L and 33R, as shown in FIG. 6, the testee 2 can adjust the position of the device main body 5 so that the pupils 9L and 9R are positioned at the center of the left and right display frames 33L and 33R, respectively.

In this embodiment, as a preferable example, the synthesized image of the left and right eyes 8L and 8R obtained by the above synthesis processing is displayed on both of the display devices 12L and 12R. However, this synthesized image may be displayed on only one of the display devices or may be alternately displayed on the left and right display devices.

<4. Effect of the Embodiment>

According to the vision testing device 1 of this embodiment, the following effect can be obtained.

(1) When the device main body 5 is mounted on the head 3 of the testee 2 using the mounting fixture 6, the testee 2 himself/herself can recognize a positional displacement state of the eyeball 8 caused by the positional displacement of the device main body 5, by displaying the image of the eyeball 8 imaged by the imaging device 16 on the display device 12. Further, when the device main body 5 is mounted in a displaced state, the testee 2 himself/herself can adjust the position of the device main body 5 while viewing the image displayed on the display device 12. Therefore, an adjustment work can be ended in a shorter time as compared with a case where the testee 2 adjusts the position of the device main body 5 after an instruction is received from the tester as in a conventional case. Further, when adjusting the position of the device main body 5, the tester does not need to give an instruction to the testee 2 or check the positional displacement while watching the monitor. Therefore, it is possible to reduce the workload of the tester involved in the positional adjustment fo the device main body 5. Further, the tester can perform other work (for example, setting of test items and test conditions, etc.) until the testee 2 ends the positional adjustment of the device main body 5. Accordingly, a medical work related to the vision test can be efficiently advanced.

(2) By setting the display frame 33 on the display surface 12a of the display device 12 and displaying the image of the eyeball 8 in the display frame 33, the testee 2 himself/herself can recognize the positional displacement state of the eyeball 8 caused by the positional displacement of the device main body 5, from the pupil position of the eyeball 8 in the display frame 33. Further, from the positional relationship between the display frame 33 and the pupil 9, the testee 2 can intuitively grasp in which direction the position of the eyeball 8 is displaced in the display frame 33 to what extent.

(3) By displaying the mark 35 in the display frame 33 of the display surface 12a, the testee 2 can more accurately grasp in which direction the position of the eyeball 8 is displaced in the display frame 33 to what extent, from the positional relationship between the pupil 9 and the mark 35 displayed in the display frame 33.

(4) The optical axis 18a from the eyeball position to the mirror 20 is shared by the display optical system 11 and the observation optical system 15. Therefore, when the image of the eyeball 8 imaged by the imaging device 16 is displayed on the display device 12, an amount of positional displacement of the device main body 5 can be directly reflected on a displacement amount of the eyeball 8 (pupil 9). Accordingly, when the testee 2 adjusts the position of the device main body 5, how much adjustment should be made can be accurately and easily grasped from the image of the eyeball 8 displayed on the display device 12.

<5. Other Embodiment>

Figure 9:
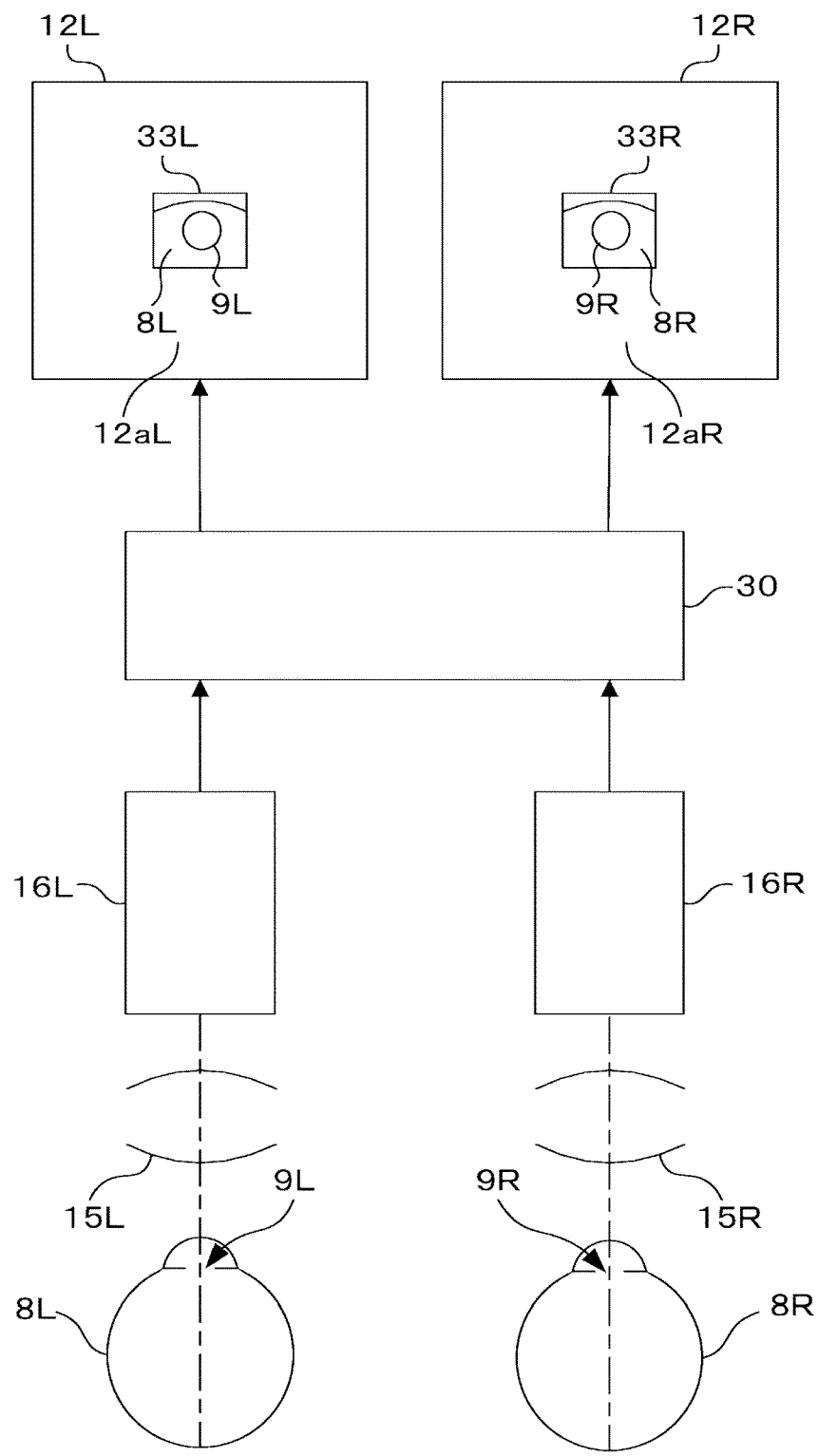
FIG. 9 is a view for explaining another embodiment of the present invention.

This embodiment is different from the previous embodiment in a state in which the vision testing device 1 is operated in the alignment mode. That is, in the alignment mode, the controller 30 displays the images of the left and right eyeballs 8 one by one to the testee 2 who is wearing the device main body 5. Specifically, as shown in FIG. 9, the controller 30 displays the image of the left eye 8L imaged by the imaging device 16L on the left-side display device 12L while displaying the image of the right eye 8R imaged by the imaging device 16R on the right-side display device 12R.

Further, the controller 30 sets the display frame 33L on the display surface 12aL of the display device 12L and displays the image of the left eye 8L in the display frame 33L. Similarly, a display frame 33R is set on the display surface 12aR of the display device 12R, and an image of the right eye 8R is displayed in the display frame 33R. The display frame 33L is set at the center of the display surface 12aL, and the display frame 33R is set at the center of the display surface 12aR. The display frame 33L for the left eye is set so that the pupil 9L of the left eye 8L imaged by the imaging device 16L is positioned at the center of the display frame 33L when the device main body 5 is properly mounted on the head 3 of the testee 2, and the testee 2 looks straight ahead using the left eye 8L. Similarly, the display frame 33R for the right eye is set so that the pupil 9R of the right eye 8R imaged by the imaging device 16R is positioned at the center of the display frame 33R when the device main body 5 is properly mounted on the head of the testee 2, and the testee 2 looks straight ahead using the right eye 8R.

In this case as well, if necessary, the mark 35 (see FIG. 4) for aligning the position of the pupil 9 of the eyeball 8 may be displayed in the display frame 33. Specifically, a mark 35L for aligning the position of the pupil 9L of the left eye 8L may be displayed at the center of the display frame 33L of the display device 12L, and a mark 35R for aligning the position of the pupil 9R of the right eye 8R may be displayed at the center of the display frame 33R of the display device 12R.

In the vision testing device having the abovementioned configuration, prior to the start of the vision test, the positional adjustment of the device main body 5 mounted on the head 3 of the testee is performed as follows.

First, the controller 30 displays the image of the left eye 8L imaged by the left-side imaging device 16L on the display device 12L, while displaying the image of the right eye 8R imaged by the right-side imaging device 16R, on the display device 12R. At this time, the controller 30 displays the image of the left eye 8L in the display frame 33L set on the display surface 12aL of the display device 12L, and displays the image of the right eye 8R in the display frame 33R set on the display surface 12aR of the display device 12R. As a result, the testee 2 who is wearing the device main body 5 on the head 3 views the image of the left eye 8L displayed in the display frame 33L of the display device 12L using the left eye 8L, while viewing the image of the right eye 8R displayed in the display frame 33R of the display device 12R using the right eye 8R.

In such a situation, the tester gives an instruction to the testee 2 to gaze left or right, for example the center of the display frame 33L of the display device 12L using the left eye 8L. At this time, when the mark 35L is displayed at the center of the display frame 33L, the instruction may be given to the testee to view this mark 35L using the left eye 8L. Thus, the line of sight of the left eye 8L of the testee 2 is fixed in a state that the line of sight is directed straight ahead. Under such a fixation state, the tester asks the testee 2 himself/herself to check which part of the display frame 33L displays the pupil 9L of the left eye 8L of the testee 2.

Next, the tester gives an instruction to the testee 2 to gaze the center of the display frame 33R of the display device 12R using the right eye 8R. At this time, when the mark 35R is displayed at the center of the display frame 33R, an instruction may be given to gaze this mark 35R using the right eye 8R. As a result, the line of sight of the right eye 8R of the testee 2 is fixed in a state that the line of sight is directed straight ahead. Under such a fixation condition, the tester asks the testee 2 himself/herself to check which part of the display frame 33R displays the pupil 9R of the right eye 8R of the testee 2.

Then, when the pupil 9L of the left eye 8L is displaced from the center of the display frame 33L or the pupil 9R of the right eye 8R is displaced from the center of the display frame 33R, an instruction is given to the testee 2 to solve the displacement by properly moving the device main body 5. Thus, for example when the position of the pupil 9L of the left eye 8L displayed in the display frame 33L and the position of the pupil 9R of the right eye 8R displayed in the display frame 33R are both displaced upward within the display frames 33L and 33R, the testee 2 moves the device main body 5 to the opposite side (downward) thereof. Further, when the position of the pupil 9L of the left eye 8L displayed in the display frame 33L and the position of the pupil 9R of the right eye 8R displayed in the display frame 33R are both displaced to the left-side in the display frames 33L and 33R, the testee 2 moves the device main body 5 on the opposite side (right-side) thereof. Further, when the position of the pupil 9L of the left eye 8L displayed in the display frame 33L is displaced upward within the frame and the position of the pupil 9R of the right eye 8R displayed in the display frame 33R is displaced downward within the frame, the device main body 5 is moved so that the left-side of the device main body 5 is tilted downward and the right-side is tilted upward. Thereby, the device main body 5 can be adjusted to a proper position. When the image of the left eye 8L is displayed on the display device 12L, one display device 12R may be set in non-display state, and when the image of the right eye 8R is displayed on the display device 12R, one display device 12L may be set in non-display state.

<6. Modified Example, Etc.>

The technical scope of the present invention is not limited to the abovementioned embodiment, but includes various modifications and improvements within the scope of deriving the specific effects obtained by the constituent features of the invention and combinations thereof.

For example, in the abovementioned embodiment, the mounting fixture 6 of the vision testing device 1 is configured by using the belts 13 and 14. However, any type of mounting fixture 6 may be adopted as long as the device main body 5 can be mounted on the head 3 of the testee 2. However, if the position of the device main body 5 moves during the vision test, a correct test result can not be obtained. Therefore, as the configuration of the mounting fixture 6, it is preferable that the device main body 5 be properly fixed to the head 3 of the testee 2.

Further, in the abovementioned embodiment, the image of the eyeball 8 imaged by the imaging device 16 is displayed as it is on the display device 12. However, the present invention is not limited thereto, and for example, the image of the eyeball 8 imaged by the imaging device 16 may be schematically formed and displayed on the display device 12. As a specific example of schematically forming the image of the eyeball 8, it is conceivable that a contour of a pupil included in the image is displayed in a circle, and the circle (the center of the pupil) is indicated by a cross line.

Further, in the abovementioned embodiment, it is assumed that the testee 2 views the visual target in infinite distance vision. However, the present invention is not limited thereto, and when the testee 2 views the visual target in near vision, each optical system is set so as to allow the testee 2 to recognize an image of a short distance in consideration of an inset amount at that time, and the left and right optical systems may be tilted inward according to the distance. Alternatively, the fixation target and the display image may be displayed closely to the inside.

Further, in the abovementioned embodiment, the liquid crystal display device is used to constitute the display device 12. However, the present invention is not limited thereto, and an organic EL (Electro Luminescence) display device may be used.

Further, in the abovementioned embodiment, the display optical system 11 is composed of four lenses in total and the observation optical system 15 is composed of two lenses in total (one of which is shared with the display optical system 11). However, the number and the shape of the lenses constituting each optical system, the lens interval in the optical axis direction, and the like can be changed as necessary. However, in order to correct the chromatic aberration and the image magnification by combining the lens having a positive power and the lens having a negative power, the second lens group 21 is preferably composed of a plurality of lenses. Further, the mirror 20 may be formed of a dichroic mirror.

Figure 10:
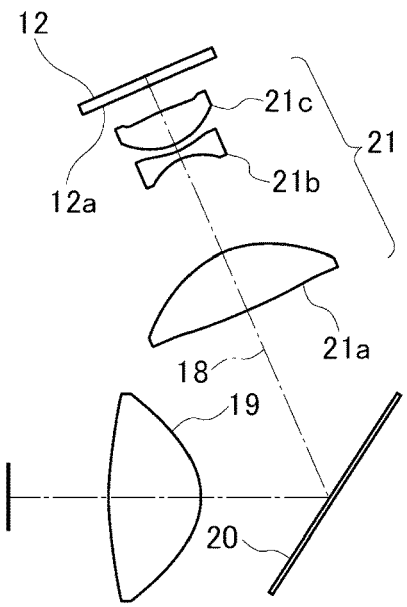
FIG. 10 is a schematic view (part 1) showing another configuration example of a display optical system.
Figure 11:
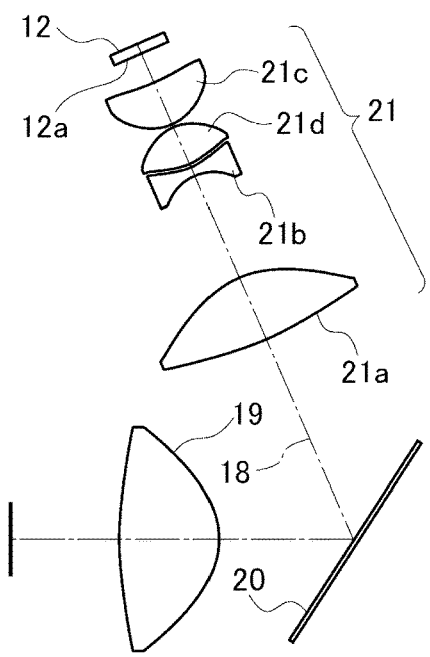
FIG. 11 is a schematic view (part 2) showing another configuration example of the display optical system.

As an example, another configuration example of the display optical system is shown in FIG. 10 and FIG. 11.

In FIG. 10, the lens 21c belonging to the second lens group 21 of the display optical system 11 is made movable in the optical axis direction by a lens moving mechanism (not shown), which is different from the above embodiment. When this configuration is adopted, the diopter can be adjusted according to the visual acuity of the testee.

On the other hand, in FIG. 11, the point that the second lens group 21 of the display optical system 11 is configured by using four lenses 21a to 21d in total by adding a lens (convex lens) 21d, and the point that the size of the display surface 12a of the planar display device 12 is reduced, are different from the abovementioned embodiment. When this configuration is adopted, the visual target can be displayed more clearly for the testee. Further, in this configuration as well, by making the lens 21c movable in the direction of the optical axis, the diopter can be adjusted according to the visual acuity of the testee.

Further, the present invention can be embodied not only as a vision testing device but also as a head-mount type display device (Head Mounted Display). In such a case, as a configuration of the head-mount type display device, "testee" is replaced with "user". Therefore, the eyeball 8 of the user using the head-mount type display device is placed at the eyeball position. Further, an image is displayed on the display surface 12a of the display device 12, instead of the visual target. The image displayed on the display surface 12a is not particularly limited and may be any of still images, moving images (games, movie images, etc.). Further, the image to be displayed is not limited to a two-dimensional image but may be a three-dimensional image.

According to the head-mount type display device to which the present invention is applied, when the device main body 5 is mounted on the head of the user using the mounting fixture 6, the user can recognize the displacement of the mounting position and can perform positional adjustment of the device main body 5. Therefore, when the user who is wearing the device main body 5 views the image on the display device 12, a relative positional relationship between the eyeball 8 of the user and the display device 12 can be properly set by performing positional adjustment of the device main body 5 prior to viewing the image on the display device 12.

DESCRIPTION OF SIGNS AND NUMERALS

1 Vision testing device
2 Testee
3 Head
5 Device main body
6 Mounting fixture
8 Eyeball
9 Pupil
11 Display optical system
12 Display device
12a Display surface
15 Observation optical system
16 Imaging device
30 Controller
33 Display frame
34 Fixation target
35 Mark

The invention claimed is:

1. A vision testing device, which is a head-mount type vision testing device mounted on a testee's head, comprising:
   a device main body having a display device for displaying a visual target for the testee and an imaging device for imaging an eyeball of the testee;
   a mounting fixture for mounting the device main body on the testee's head; and
   a controller that displays an image of the eyeball imaged by the imaging device on the display device, so that the testee can recognize a positional displacement state of an eyeball caused by a positional displacement of the device main body mounted on the testee's head using the mounting fixture.

2. The vision testing device according to claim 1, wherein the controller sets a display frame on a display surface of the display device and displays an image of the eyeball imaged by the imaging device on the display frame.

3. The vision testing device according to claim 2, wherein the controller displays a mark in the display frame for aligning a position of a pupil of the eyeball.

4. The c testing device according to claim 3 comprising:
   a display optical system provided on an optical axis between an eyeball position where the eyeball of the testee is placed and the display device; and
   an observation optical system provided on an optical axis between the eyeball position and the imaging device,
   wherein the display optical system is formed by arranging a first lens, a mirror having wavelength selectivity, and a second lens group sequentially on an optical axis from the eyeball position he display device, and
   the observation optical system is formed by arranging the first lens, the mirror, and a third lens sequentially on an optical axis form the eyeball position to the imaging device, and the optical axis from the eyeball position to the mirror is shared with the display optical system.

5. The vision testing device according to claim 2, comprising:
   a display optical system provided on an optical axis between an eyeball position where the eyeball of the testee is placed and the display device; and
   an observation optical system provided on an optical axis between the eyeball position and the imaging device,
   wherein the display optical system is formed by arranging a first lens, a mirror having wavelength selectivity, and a second lens group sequentially on an optical axis from the eyeball position to the display device, and
   the observation optical system is formed by arranging the first lens, the mirror, and a third lens sequentially on an optical axis form the eyeball position to the imaging device, and the optical axis from the eyeball position to the mirror shared with the display optical system.

6. The vision testing device according to claim 1, wherein the display device and the imaging device are separately provided for a left eye and a right eye of the testee, the controller synthesizes an image of the left eye imaged by the imaging device for the left eye, and an image of the right eye imaged by the imaging device for the right eye so as to be arranged side by side, and the synthesized images of the left and right eyes are displayed on the display device for the left eye and the display device for the right eye, respectively.

7. The vision testing device according to claim 6, wherein the controller sets two display frames side by side on the display surface of the display device for the left eye and the display surface of the display device for the right eye respectively, and displays the image of the left eye on a left-side display frame, and displays the image of the right eye on a right-side display frame viewed from the testee.

8. The vision testing device according to claim 7, wherein the controller displays a fixation target to be gazed by the testee between the image of the left eye and the image of the right eye.

9. The vision testing device according to claim 8, comprising:
a display optical system provided on an optical axis between an eyeball position where the eyeball of the testee is placed and the display device; and
an observation optical system provided on optical axis between the eyeball position and the imaging device,
wherein the display optical system is formed by arranging a first lens, a mirror having wavelength selectivity, and a second lens group sequentially on an optical axis from the eyeball position to the display device, and
the observation optical system is formed by arranging the first lens, the mirror, and a third lens sequentially on an optical axis form the eyeball position to the imaging device, and the optical axis from the eyeball position to the mirror is shared with the display optical system.

10. The vision testing device according to claim 7, wherein the controller displays a mark in the display frame for aligning a position of a pupil of the eyeball.

11. The vision testing device according to claim 10, comprising:
a display optical system provided on an optical axis between an eyeball position where the eyeball of the testee is placed and the display device; and
an observation system provided on an optical axis between the eyeball position and the imaging device,
wherein the display optical system is formed by arranging a first lens, a mirror having wavelength selectivity, and a second lens group sequentially on an optical axis from the eyeball position to the display device, and
the observation optical system is formed by arranging the first lens, the mirror, and a third lens sequentially on an optical axis form the eyeball position to the imaging device, and the optical axis from the eyeball position to the mirror is shared with the display optical system.

12. The vision testing device according to claim 7, comprising:
a display optical system provided on an optical axis between an eyeball position where the eyeball of the testee is placed and the display device; and
an observation optical system provided on an optical axis between the eyeball position and the imaging device,
wherein the display optical system is formed by arranging a first lens, a mirror having wavelength selectivity, and a second lens group sequentially on an optical axis from the eyeball position to the display device, and
the observation optical system is formed by arranging the first lens, the mirror, and a third lens sequentially on an optical axis form the eyeball position to the imaging device, and the optical axis from the eyeball position to the mirror is shared with the display optical system.

13. The vision testing device according to claim 6, wherein the controller displays a fixation target to be gazed by the testee between the image of the left eye and the image of the right eye.

14. The vision testing device according to claim 13, comprising:
a display optical system provided on an optical axis between an eyeball position where the eyeball of the testee is placed and the display device; and
an observation optical system provided on an optical axis between the eyeball position and the imaging device,
wherein the display optical system is formed by arranging a first lens, a mirror having wavelength selectivity, and a second lens group sequentially on an optical axis from the eyeball position to the display device, and
the observation optical system is formed by arranging the first lens, the mirror, and a third lens sequentially on an optical axis form the eyeball position to the imaging device, and the optical axis from the eyeball position to the mirror is shared with the display optical system.

15. The testing device according to claim 6, comprising:
a display optical system provided on an optical axis between an eyeball position where the eyeball of the testee is placed and the display device; and
an observation optical system provided on an optical axis between the eyeball position and the imaging device,
wherein the display optical system is formed by arranging a first lens, a mirror having wavelength selectivity, and a second lens group sequentially on an optical axis from the eyeball position to the display device, and
the observation optical system is formed by arranging the first lens, the mirror, and a third lens sequentially on an optical axis form the eyeball position to the imaging device, and the optical axis from the eyeball position to the mirror is shared with the display optical system.

16. The vision testing device according to claim 1, comprising:
a display optical system provided on an optical axis between an eyeball position where the eyeball of the testee is placed and the display device; and
an observation optical system provided on an optical axis between the eyeball position and the imaging device,
wherein the display optical system is formed by arranging a first lens, a mirror having wavelength selectivity, and a second lens group sequentially on an optical axis from the eyeball position to the display device, and
the observation optical system is formed by arranging the first lens, the mirror, and a third lens sequentially on an optical axis form the eyeball position to the imaging device, and the optical axis from the eyeball position to the mirror is shared with the display optical system.

17. A head-mount type display device, which is a head-mount type vision testing device mounted on a user's head, comprising:
a device main body having a display device for displaying an image for the user, and an imaging device for imaging an eyeball of the user;
a mounting fixture for mounting the device main body on the user's head; and
a controller that displays an image of the eyeball imaged by the imaging device on the display device, in order that the user can recognize a positional displacement state of an eyeball caused by a positional displacement of the device main body mounted on the user's head using the mounting fixture.

* * * * *